United States Patent [19]
Maitland et al.

[11] Patent Number: 6,102,917
[45] Date of Patent: Aug. 15, 2000

[54] SHAPE MEMORY POLYMER (SMP) GRIPPER WITH A RELEASE SENSING SYSTEM

[75] Inventors: Duncan J. Maitland, Pleasant Hill; Abraham P. Lee, Walnut Creek; Daniel L. Schumann, Concord; Luiz Da Silva, Danville, all of Calif.

[73] Assignee: The Regents of the University of California, Oakland, Calif.

[21] Appl. No.: 09/116,019

[22] Filed: Jul. 15, 1998

[51] Int. Cl.⁷ .................................................. A61F 11/00
[52] U.S. Cl. ........................................ 606/108; 606/200
[58] Field of Search .......................... 606/108, 190–192, 606/205–208, 200

[56] References Cited

U.S. PATENT DOCUMENTS

| | | | |
|---|---|---|---|
| 4,520,816 | 6/1985 | Schachar et al. | 128/303.1 |
| 4,899,741 | 2/1990 | Bentley et al. | 606/27 |
| 5,108,407 | 4/1992 | Geremia et al. | 606/108 |
| 5,578,074 | 11/1996 | Mirigian | 606/108 |
| 5,601,600 | 2/1997 | Ton | 606/191 |
| 5,645,564 | 7/1997 | Northrup et al. | 606/205 |
| 5,911,737 | 6/1999 | Lee et al. | 606/209 |
| 5,989,242 | 11/1999 | Saadat et al. | 606/151 |

OTHER PUBLICATIONS

G. Geremia et al., Embolization of Experimentally Created Aneurysms with a Laser–Activated Detachable Coil Device, UNR, Am. J. Neuroradiol 19:566–569, Mar. 1998.

*Primary Examiner*—Michael Buiz
*Assistant Examiner*—Jonathan D. Goldberg
*Attorney, Agent, or Firm*—L. E. Carnahan; Alan H. Thompson

[57] ABSTRACT

A system for releasing a target material, such as an embolic coil from an SMP located at the end of a catheter utilizing an optical arrangement for releasing the material. The system includes a laser, laser driver, display panel, photodetector, fiber optics coupler, fiber optics and connectors, a catheter, and an SMP-based gripper, and includes a release sensing and feedback arrangement. The SMP-based gripper is heated via laser light through an optic fiber causing the gripper to release a target material (e.g., embolic coil for therapeutic treatment of aneurysms). Various embodiments are provided for coupling the laser light into the SMP, which includes specific positioning of the coils, removal of the fiber cladding adjacent the coil, a metal coating on the SMP, doping the SMP with a gradient absorbing dye, tapering the fiber optic end, coating the SMP with low refractive index material, and locating an insert between the fiber optic and the coil.

20 Claims, 4 Drawing Sheets

SHAPE MEMORY POLYMER (SMP) GRIPPER WITH A RELEASE SENSING SYSTEM

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to microfabricated therapeutic actuators, particularly to therapeutic actuators utilizing shape memory polymer (SMP) tubing and microtubing as a gripper/release mechanism, and more particularly to an SMP gripper with a release sensing system and coupling arrangements for directing light into the SMP.

Microactuators for remote and precise manipulation of small objects is of great interest in a wide variety of applications. Recently substantial efforts have been directed to the development of microactuators or microgrippers for use in the medical field, such as for catheter-based intervention therapies. There has been particular interest in the development of microactuators capable of operating in small (250–500 $\mu$m) diameter applications, such as in blood vessels in the human brain, which enable catheter-based devices to reach and treat an aneurysm in the brain.

One recent approach to satisfying this need involves microactuators or microgrippers fabricated by using known silicon-based techniques or precision micromachining, or a combination of these techniques, with the microgrippers being actuated, for example, by balloons or by shape-memory alloy (SMA) films or wires deposited on or connected to the jaws of the microgrippers. Such an approach is described and claimed in U.S. Pat. No. 5,645,564 issued Jul. 8, 1997. Another recent approach involves a miniature plastic gripper constructed of either heat-shrinkable or heat-expandable plastic tubing having a cut in one end section to form gripping surfaces or jaws which are moved by inflation or deflation of an associated microballoon. Such an approach is described and claimed in U.S. Pat. No. 5,609,608 issued Mar. 11, 1997.

Patients with potentially life-threatening hemorrhagic brain aneurysms are in need of a safe, reliable, and fast release mechanism for the deposition of embolic platinum coils via catheters, such as the commercially available Guglielmi Detachable Coil (GDC). The GDC utilizes the electrolytical dissolution of a designated guidewire junction to generate the release action. This procedure typically takes 10–30 minutes and is difficult to control in a reliable fashion. Also, the effects of the dissolved material into the blood stream are a potential hazard to the patient.

A recent approach to overcome the GDC problems is to provide a delivery/release mechanism based on SMP, a polyurethane-based material that undergoes a phase transformation at a manufactured temperature (Tg) of choice. After the material is polymerized (cross-linked), the material is molded into its memory shape. At temperatures above Tg, the material can be easily reshaped into another configuration, and upon cooling below the Tg the new shape is fixed, but upon increasing the temperature to above the Tg, the material will return to its original memory shape. By inserting a GDC, for example, into an end of a SMP microtube heated to a temperature above its Tg, applying pressure to the outside of the SMP microtube to shape the tube about an end of the GDC, and then lowering the temperature below the Tg, the GDC is secured and retained in the microtube. After inserting the microtube and retained GDC via a catheter to a desired location, the SMP microtube is locally heated to above the Tg and it returns to its original shape releasing the GDC, after which the microtube is withdrawn leaving the GDC in place, without releasing any dissolved materials, etc., into the blood stream. Such an approach is described and claimed in copending U.S. application Ser. No. 08/807,412 filed Feb. 28, 1997, now U.S. Pat. No. 5,911,737 issued Jun. 15, 1999, entitled "Microfabricated Therapeutic Actuators," and assigned to the same assignee.

A more recent approach which utilizes SMP microtubing as a retention/release means for material, such as an embolic coil, provides various mechanisms for heating and cooling the SMP microtubing, including resistive heating, optical heating, and external field (RF, magnetic induction) heating, and coatings of selected materials on the microtubing. This approach is described and claimed in copending U.S. application Ser. No. 09/067,824 filed Apr. 28, 1998, entitled "Microfabricated Therapeutic Actuators and Release Mechanisms Therefor," assigned to the same assignee.

The present invention utilizes SMP tubing or microtubing as the retention/release means, as in the above-referenced copending applications, but using a laser light/fiber optic approach for releasing a coil, for example, from the SMP microtubing, a feedback or sensing system to confirm release of the coil, and coupling mechanisms of light into the SMP microtubing for heating same. The features of the present invention are incorporated into a complete catheter system, which includes a laser and control, a display panel, fiber optic components and coupler, the SMP gripper, and a release sensing or feedback arrangement.

SUMMARY OF THE INVENTION

It is an object of the present invention to provide an SMP gripper release mechanism.

A further object of the invention is to provide an SMP microgripper release mechanism with means for confirming release of a material from the gripper.

A further object of the invention is to provide a catheter system for depositing an embolic coil for treatment of brain aneurysms, for example, using an SMP gripper with an optical release and release confirmation arrangement.

A further object of the invention is to provide an SMP microgripper with an optical release mechanism with various approaches for coupling light in the SMP material for heating same causing release of an object therefrom.

Another object of the invention is to provide a catheter system with an optically activated SMP microgripper release having a feedback arrangement to confirm release of an object from the microgripper.

Another object of the invention is to provide a catheter system with an optically activated SMP microgripper release having a light coupling arrangement whereby light is more effectively absorbed by the SMP microgripper, which enables quicker release of an object therefrom.

Another object of the invention is to provide a catheter system with an optically activated SMP microgripper, which receives light energy from a laser via an optical fiber arrangement, and which includes a coupler which receives reflected light from the microgripper and directs same into a photodetector and to a panel display for confirming release of an object from the microgripper.

Other objects and advantages of the present invention will become apparent from the following description and accompanying drawings. Basically, the invention involves an SMP microgripper or gripper release system with sensing of an object release, such as an embolic coil, from the microgripper. The SMP microgripper is provided with an optical release mechanism, including a laser light source and a fiber optic system connected to the microgripper. The fiber optic system includes a coupler, which receives a small amount of the laser light reflected from the optic fiber-coil interface and which is directed into a photodetector to a display panel. As the laser light heats the SMP material of the microgripper section retaining to the coil, the coil is released. The coil movement causes the reflected light signal to decrease as the coil-optic fiber distance increases. The signal may decrease for a second physical reason, as well. With diffusing fibers, which is close to the production design, the reflected light also decreases due to less reflection at the diffuse-fiber-surface/SMP interface. As the SMP expands, the interface becomes diffuse-fiber-surface/body fluid that early experiments have shown to be less reflective. This change in the reflected light signal is used to confirm release of the coil and to control the driving current of the laser. The SMP microgripper and associated optic fiber for heating same to release the coil includes various light coupling arrangements to assure more effective heating of the object (coil) retaining section of the microgripper.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The present invention is directed to a system which involves depositing a material or object, such as an embolic coil, in a remote location, such as in an artery of the human body, using an SMP microgripper or gripper having an optical release mechanism coupled to a feedback arrangement for confirming the release of the object from the microgripper. The optical release mechanism included an optic fiber fixedly secured to one end of an SMP microgripper to cause heating via a laser light source of an unsecured end of the microgripper to cause release therefrom of the object retained therein. It is to be understood that the object (coil) retained in the SMP microgripper can be loaded therein using the same optical system by heating the object retaining end of the SMP microgripper to above a selected temperature (Tg), then applying pressure to the heated SMP material causing it to form around the coil, and then cooling the SMP material to a temperature below the Tg, which retains the coil in the end of the SMP microgripper, as described in greater detail in the above-referenced copending applications.

While above-referenced copending application Ser. No. 09/067,824 utilizes an optical arrangement for heating a dye-filled chamber which heats an SMP microtubing to enable the loading of an object (coil) to be retained therein, the present invention expands the optical system with emphasis on the release of the object from the SMP microgripper, although this same system could be used to load the object. The primary advance provided by the present invention in the optical release system is a sensor subsystem used to confirm release of the object, as described with respect to FIG. 1, and in various light coupling arrangements described with respect to FIGS. 4–11, which more effectively transmit the light into the SMP to heat same more uniformly. Thus, by use of the present invention, the time period for release of the coil (10–30 minutes for the GDC) is reduced to about 1 second, and the coil release mechanism additionally provides feedback relative to the actual release of the coil. While the following description exemplifies the depositing of an embolic coil via a catheter system, the invention may be utilized to deposit any object, target material, medicine, etc., at a remote location.

Figure 1:
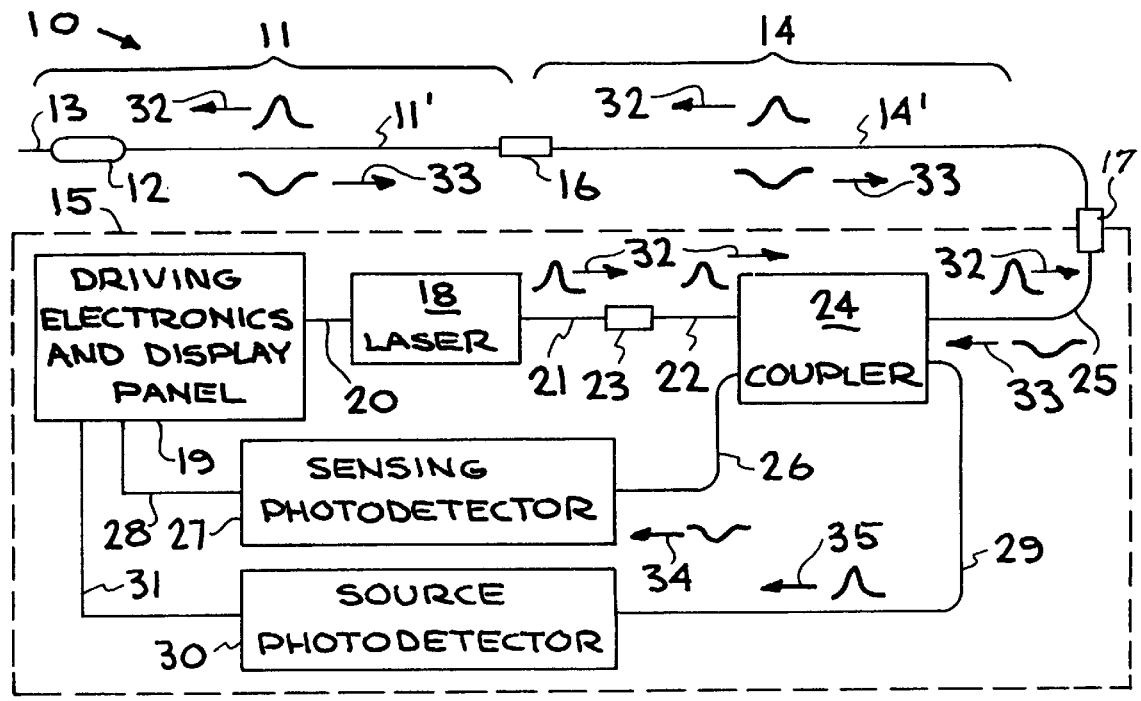
FIG. 1 schematically illustrates a catheter system incorporating the present invention.

Referring now to the drawings, FIG. 1 schematically illustrates a system incorporating the invention, which involves an embolic coil release catheter. The system, generally indicated at 10, comprises a catheter section 11, which includes an optic fiber 11' having at one end an SMP microgripper 12 retaining a deposit material, such as a coil 13, and connected at the other end to an extension section 14, including an optic fiber 14' connected to a control unit generally indicated at 15. The catheter section 11, extension section 14, and control unit 15 are interconnected by optic fiber connectors 16 and 17. Control unit 15 includes a laser 18, laser control or driving electronics and display panel assembly generally indicated at 19, and connected as indicated at 20 to laser 18. Laser 18 is connected by optic fibers 21 and 22 via an optic fiber connector 23 to a fiber optic coupler 24, such as a conventional 90/10 optical coupler, which is connected via an optic fiber 25 to optic fiber connector 17. Coupler 24, wherein 90 percent of the light passes through and 10 percent is bypassed, is also connected by an optic fiber 26 to a sensing photodetector 27, which is connected to the display panel section of assembly 19 as indicated at 28. Coupler 24 is also connected by an optic fiber 29 to a source photodetector 30, which is connected to the driving electronics or control section of assembly 19, as indicated at 31. Laser light (pulsed or continuous) from laser 18 is transmitted, as indicated by pulses and arrows 32, through optic fiber 21, connector 23, optic fiber 22, coupler 24, optic fiber 25, connector 17, an optic fiber 14' in extension section 14, connector 16, and an optic fiber 11' in catheter section 11 onto an end section of SMP microgripper 12, which retains the coil 13, causing heating of the material of microgripper 12 located around the coil, as described hereinafter with respect to FIGS. 2 and 3, causing release of the coil 13 from microgripper 12. A small amount of laser light is reflected from the optic fiber 11'-coil 13 interface, as indicated by inverted pulses and arrows 33 back to the coupler 24, which is transmitted through optic fiber 26 to sending photodetector 27, as indicated by the inverted pulse and arrow 34. Coupler 24 also transmits a small amount of light from laser 18 to source photodetector 30 via optic fiber 29 as indicated by the pulse and arrow 35. Thus laser light fluctuations are monitored by the source photodetector 30, and the load/release condition of the microgripper 12 is monitored by the sensing photodetector 27. As the laser light heats an end section of the SMP microgripper 12 in the distal tip of the catheter 11, the microgripper releases the coil. The coil movement, with respect to the outer end of optic fiber 11', causes the reflected signal 33 to decrease as the coil optic fiber distance increases. The changes in the reflected signal 33 can be used to control the driving current of the laser via the coupler 24, the source photodetector 30, and the driving or control electronics of assembly 19, and the reflected signal 33 can be used to alert an operator of the status of the coil (loaded or released) via the coupler 24, the sensing photodetector 27, and the display panel of assembly 19.

Figure 2:
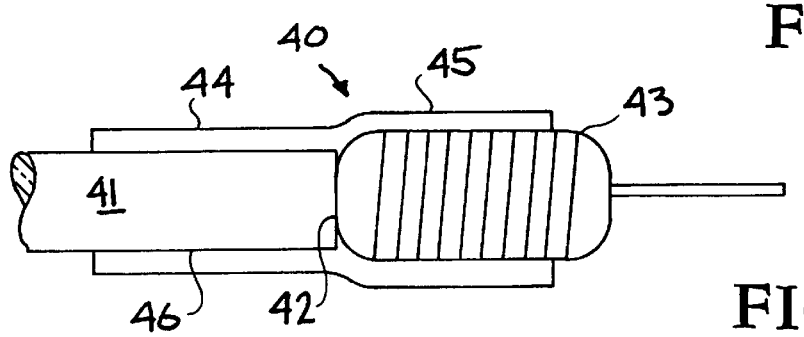
FIGS. 2 and 3 illustrate an enlarged view of the distal end of the catheter of FIG. 1 showing an SMP microgripper having an optic fiber release mechanism, with FIG. 2 showing an embolic coil retained in the microgripper, and FIG. 3 showing the coil released from the microgripper.
Figure 3:
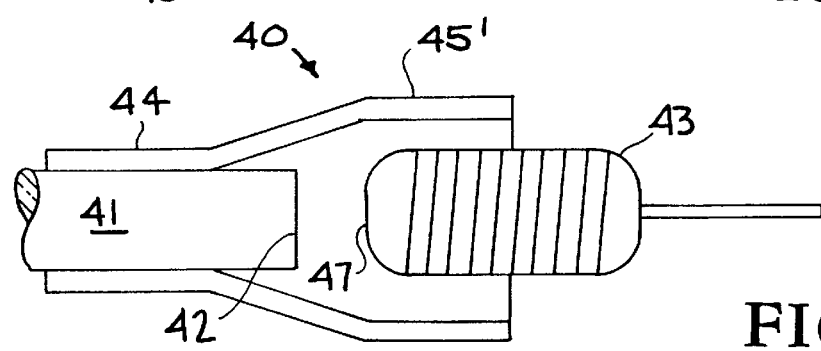

FIGS. 2 and 3 illustrate an embodiment of an SMP microgripper retaining and releasing a load or object, such as an embolic coil, the microgripper being attached to an optic fiber, as described above in FIG. 1, whereby upon release of the coil, a feedback signal enables confirmation of the release. As shown in FIG. 2, an SMP microgripper 40 connected to an end section of an optic fiber 41, having a terminal end 42, retains a deposit material (embolic coil) 43. The microgripper 40 comprises two sections 44 and 45 of different diameter, with section 44 being fixedly secured or attached, as by an adhesive layer 46 to the end section of optic fiber 41, which may, for example, be the distal tip of the optic fiber 11' of the catheter 11 of FIG. 1. End section 45 of microgripper 40 retains the coil 43. Thus, as shown in FIG. 2, the catheter, via the end of optic fiber 41, is loaded and ready for deployment. As shown in FIG. 3, the catheter of FIG. 1, for example, has been deployed such that the coil 43 is located at a desired point of use, whereby end section 45 of the SMP microgripper 40 is heated, as by laser light described above with respect to FIG. 1 via the optic fiber 41, to a temperature above its transition temperature Tg, and the end section 45 of FIG. 2 is relaxed (expanded) to its original (extruded) diameter, as indicated at 45', thereby releasing coil 43. The end section 45 of SMP microgripper remains in its expanded state after the laser-coupled thermal energy is turned off and the SMP cools below its transition temperature, and is thus ready to be reheated above the transition temperature Tg, whereby with another coil or load inserted in end section 45, the end section can be squeezed, by applied pressure, around the coil or load and cooled to a temperature below the transition temperature, whereby the SMP microgripper 40 is again loaded for deployment.

As described in detail in the above-referenced copending applications, the SMP material of the microgripper 40 can be manufactured with different transition temperatures Tg, and thus the end sections 44 and 45 of SMP microgripper 40 may be fabricated with different transition temperatures, or with the same transition temperature. If end sections 44 and 45 of the microgripper of FIGS. 2 and 3 have the same transition temperature, the difference in diameter, as shown in FIG. 2, is due to different pressures being applied to the end sections such that end section 44 retains the fiber optic 41 and end section 45 retains the coil 43. When heated, the laser light is coupled only to end section 45 and not to end section 44, and due to the adhesive layer 46, the end section 44 is not permitted to expand.

The release and deposition of the coil, as shown in FIG. 3, changes the value of the reflected signal 33 of FIG. 1, as sensed by the photodetector 27. As the coil 43 moves away from the terminal end 42 of optic fiber 41, the signal 33 reflecting from the proximal end 47 of the metallic coil 43 decreases. The decrease in reflected light 33 is measured as a time dependent decrease in light at the photodetector 27. The reflected signal 33, as it passes through coupler 24, is also directed to photodetector 30, and thus the reflected signal can be used as feedback into the controller or driving electronics for the laser, or stand alone as a load/release indicator of the microgripper. In either case, several signal processing schemes or arrangements are available to separate the signal generated by the coil release from the background noise created by other intensity changes along the optical path. The three detection schemes or arrangements described below offer the possibility of being qualitative (release or not released) or quantitative (partial release).

Figure 13:
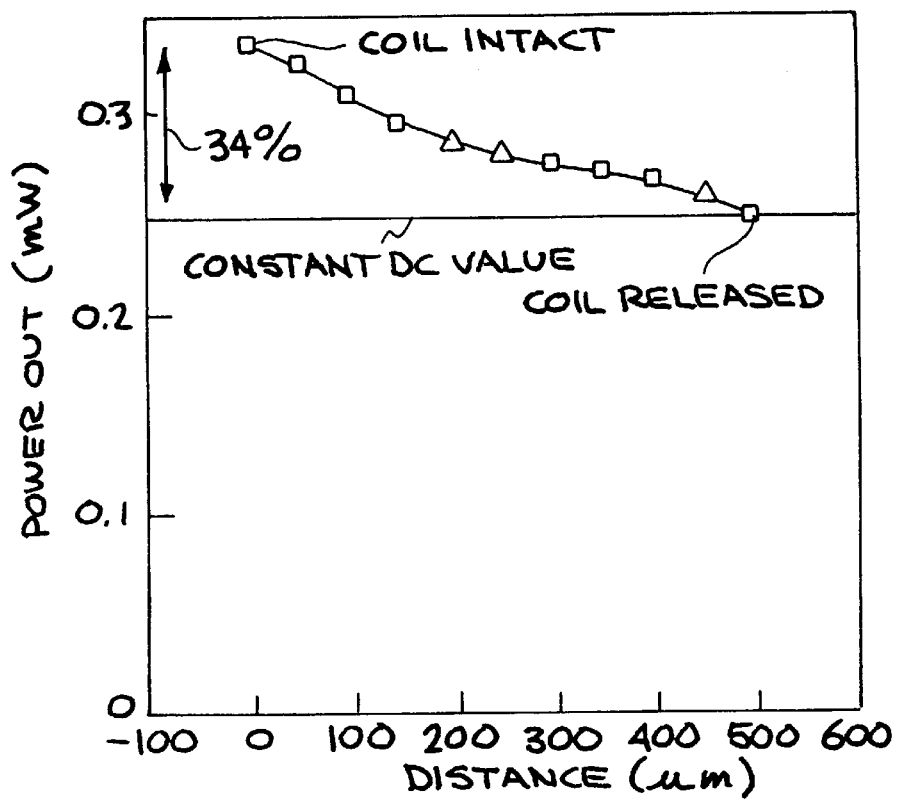
FIG. 13 graphically illustrates the sensor system of the invention for detecting release of the embolic coil from the SMP microgripper.

In the simplest scheme, a threshold DC change can be used as a detection algorithm. If the decrease in the photodetector's sensed intensity drops below a preset threshold, then the coil is interpreted as being released. FIG. 13, which is described in more detail below, presents data for the DC scheme. The influence of macrobends on the detected DC intensity was measured to be less than 5 percent of the change caused by coil release. Thus the macrobend DC intensity change was insignificant compared to the DC change caused by the coil release.

In general, however, the DC method is susceptible to noise from sources like optical connector alignment, catheter bending, and source output (although a good DC scheme would reference out source changes—the fiber coupler may have an unused output fiber that could be connected to another detector). An AC scheme would take advantage of the time-dependence of the coil as it is released. Thus electronically filtering out DC changes, an AC scheme would interpret a released coil if a low-frequency intensity change is detected. Since the coil release is expected to take place on the order of a second, the release might be characterized by frequencies from 0.1–10 Hz. The AC scheme may or may not utilize frequency lock-in techniques to reference out the DC signals. In such a scheme, the laser light source would be modulated at a reference sinusoidal frequency at low power levels (near-minimum detectable by the sensing photodetector). An electronic low pass filter would reference out the background noise and pass the signal resulting from the movement of the coil. Like the DC scheme, the AC scheme may also benefit from monitoring the source output intensity and referencing it out from the signal.

Finally, since the coil movement is on the order of 500 $\mu$m, interference techniques can be used to measure the fringe shifts caused by the coil release. Since the current implementation uses a source (laser) with a wavelength near 800 nm, the distance of 500 $\mu$m corresponds to about 625 fringes. The interference measurements are complicated by the optical losses associated with the coil release. Nonetheless, the interference between the gripper signal and a reference signal from a fixed reflection in the extra arm of the fiber coupler can be used to localize the signal to the coil release. The reference arm of an interferometer (fiber-based Michelson) can be used to reference out source intensity changes as it was in the AC and DC schemes (if the signal is partially reflected in the reference arm).

FIGS. 4–11 illustrate different embodiments or techniques for coupling the laser light from the optic fiber into the coil retaining end section of the SMP microgripper to effectively heat the SMP material of the retaining end section, causing release of the coil. The performance of the SMP microgripper depends on the coupling of the laser light into the SMP material. The laser wavelength is properly selected such that the SMP will absorb the light. This absorption can be intrinsic or extrinsic. Doping the SMP with small concentrations of dye is an example of extrinsic absorption. The absorbed light will be converted to thermal energy. The goal of the optical coupling from the optic fiber into the SMP material is to uniformly heat the SMP gripper end section along the length of the embolic coil. When uniform or near uniform coupling of light to the SMP material, material along the SMP microgripper end section will simultaneously and uniformly relax along the length of the coil releasing same, as shown in FIG. 3. Since each of FIGS. 4–11 constitute a modification of FIGS. 2–3, corresponding components will be given corresponding reference numerals.

Uniform optical coupling is best for actuating the catheter system of FIG. 1. FIGS. 4–11 show a basic coupling technique with seven coupling enhancement techniques that are available to achieve uniform light distributions in the SMP material along the length of the gripped coil. The techniques of FIGS. 4–11 can be used alone or in combination. Note that when extrinsic dyes are used, the dye concentration automatically becomes a parameter that can be used to control the coupling uniformity.

Figure 4:
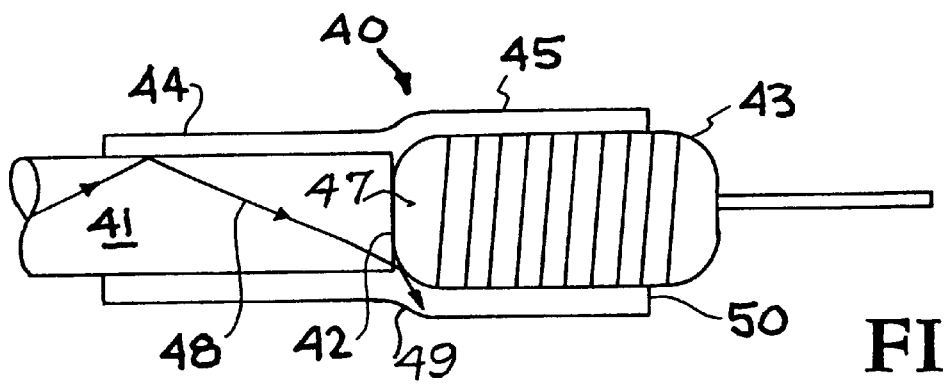
FIGS. 4–11 illustrate various light coupling mechanisms for increasing heat-distribution uniformity of the SMP material retaining the coil.

FIG. 4 illustrates a basic coupling embodiment or technique wherein the end 42 of optic fiber 41 directly butts the proximal end 47 of the embolic coil 43. The curved surface of the end 47 of coil 43 allows a light path, indicated by arrow 48, to pass into the end section 45 of the SMP microgripper 40, and light absorption results in heat generation as indicated by arrow 49 toward a distal end 50 of the SMP microgripper 40.

Figure 5:
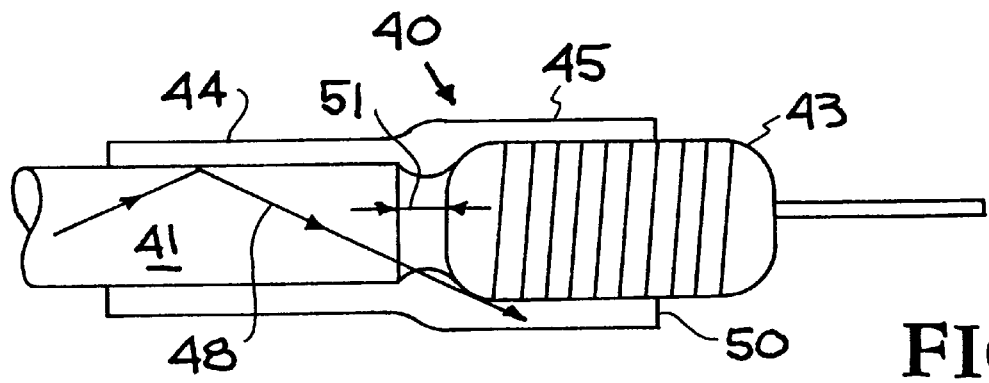

FIG. 5 shows the basic coupling technique of FIG. 4 enhanced by loading the coil 43 into the SMP microgripper 40 such that a gap 51 exists between the coil 43 and optic fiber 41. The gap 51 allows light with smaller numerical aperture to pass into the SMP gripper end section 45. For a given absorption coefficient, the result is that more light penetrates deeper toward the distal end 50 of the SMP material.

Figure 6:
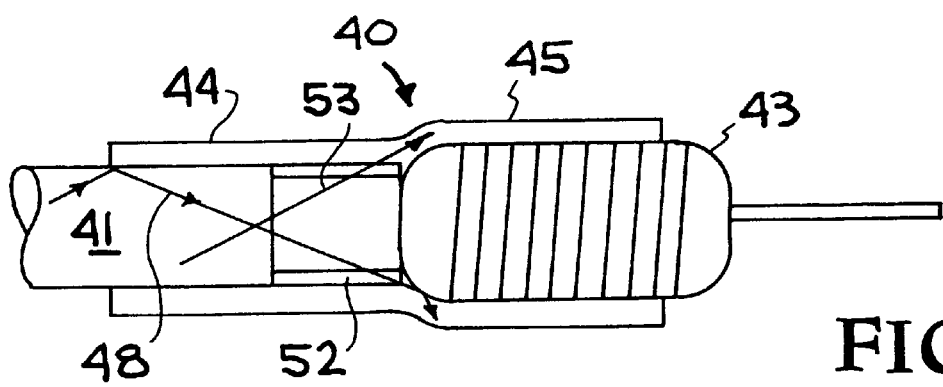

FIG. 6 enhances the basic coupling technique of FIG. 4 by removing the fiber cladding from the distal end of the optic fiber 41, as indicated at etched area 52. The cladding is removed by etching, either mechanically or chemically. The typical length of the etched area 52 is on the order of hundreds of microns. The etching 52 allows light, indicated at 53, to escape from the optic fiber 41 to the SMP-coil interface enhancing heating of the end 45 of SMP microgripper 40. For a given absorption coefficient, the result is that more light penetrates deeper toward the distal end of the SMP material.

Figure 7:
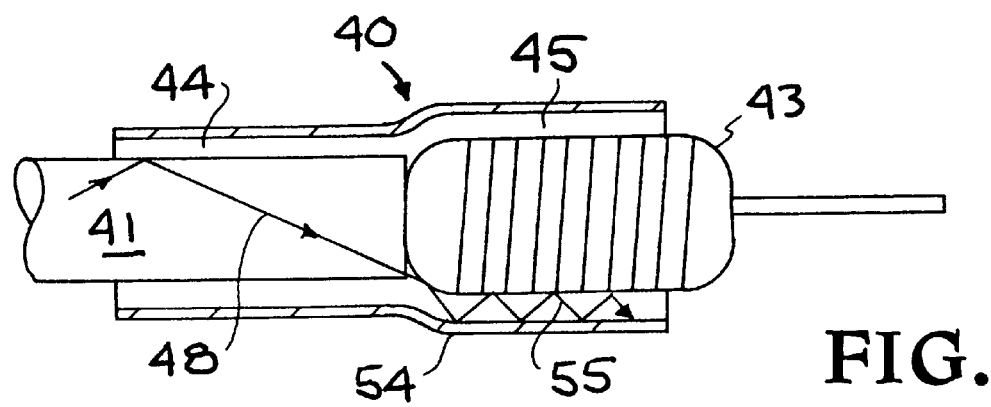

In FIG. 7, the basic coupling technique of FIG. 4 is enhanced by adding a reflective coating 54 to the SMP microgripper 40. The coating 54 may be any biocompatible metal, such as platinum, gold, or titanium, with a thickness of 250 to 500 Å. The coating acts as a mirrored surface, reflecting the nonabsorbed light, as indicated by arrow 55, toward the distal end of the SMP microgripper. For a given absorption coefficient, the result is that more light penetrates deeper toward the distal end of the SMP material.

Figure 8:
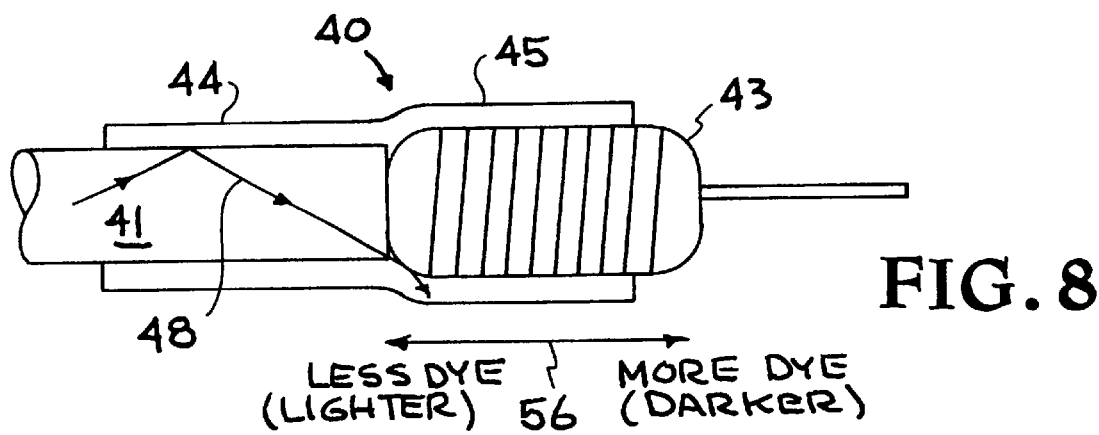

The basic coupling technique is enhanced, as shown in FIG. 8, by grading an extrinsic dye into the SMP microgripper 40 such that more light is absorbed at the distal end of the SMP material relative to the coil-optic fiber interface, as indicated by legends and arrow 56, wherein there is more dye at the distal end than at the coil-optic fiber interface. For a given light path, the absorption coefficient gradient will counter the natural exponential energy deposition of uniform absorber concentrations. The result is an increase in coupling uniformity.

Figure 9:
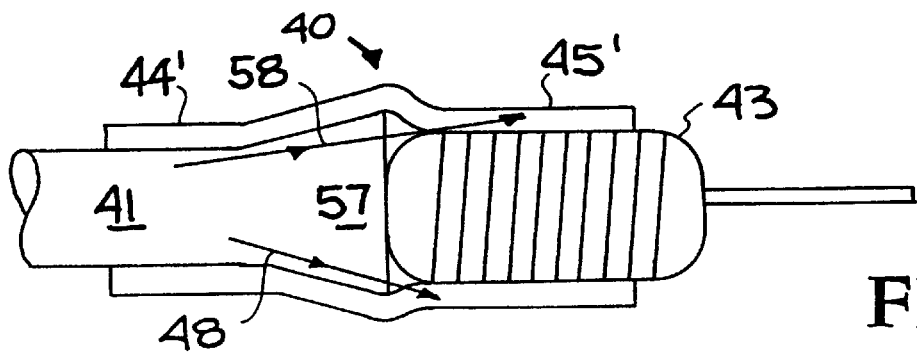

In FIG. 9, the basic coupling technique of FIG. 4 is enhanced by using an optic fiber 41 having a tapered end 57. The increased tapered angle 0 to 45° and increased diameter (up to 4× fiber diameter) of the optic fiber 41 allows more light to pass into the distal end of the SMP microgripper, as shown by arrow 58. Note that the SMP material of end sections 44' and 45' is heated, formed, and cooled to correspond to the tapered end 57 of optic fiber 41. The increased optic fiber diameter may also have mechanical advantages for releasing the coil 43.

Figure 10:
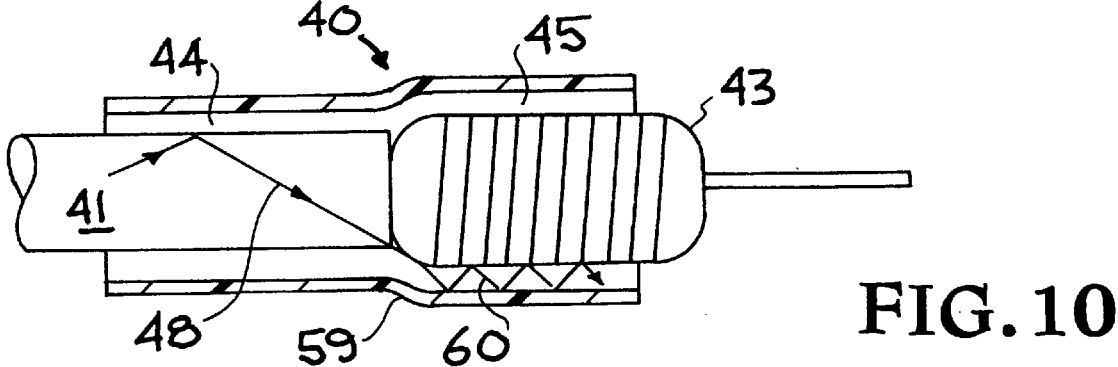

FIG. 10 provides enhancement of the basic coupling technique of FIG. 4 by coating the SMP microgripper 40 with a relatively lower refractive index material 59, such as epoxies, polyurethanes, or elastomers, having a refractive index of 1.400 to 1.500. The result is that the SMP material acts like a waveguide to light traveling toward the distal end of the SMP material, as indicated by arrow 60.

Figure 11:
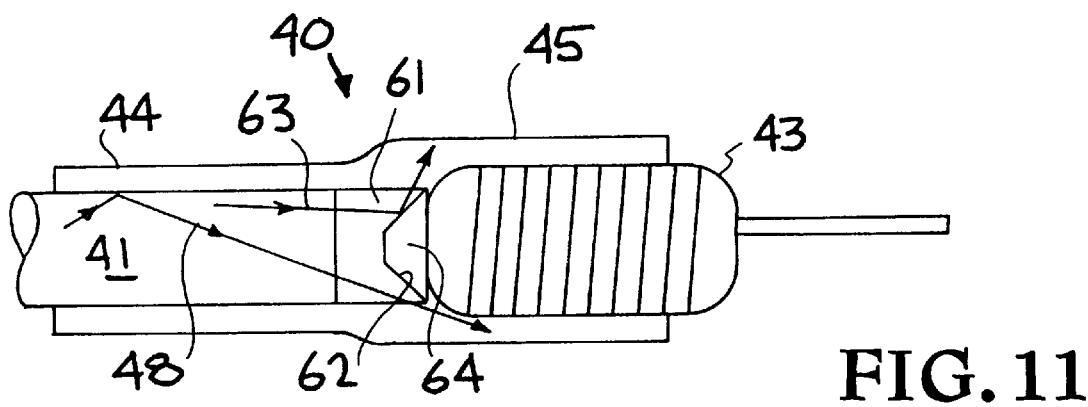

In FIG. 11, the basic coupling technique of FIG. 4 is enhanced by adding a conical insert 61 between the end 42 of optic fiber 41 and the end 47 of coil 43. The inverted cone 61 has an angled surface 62 (angle of 0 to 45°) that reflects light into the SMP material, as indicated by arrow 63, as well as creating a gap 64 that acts like the enhancement technique of FIG. 5. The insert (cone) 61 can be a preformed part that is included in the assembly of the catheter or formed during the assembly process. For example, the insert 61 may be made of SMP material or an epoxy if formed during assembly. The insert 61 will typically exhibit little or no absorption of the laser light. For a given absorption coefficient the result is that more light penetrates deeper toward the distal end of the SMP microgripper 40.

Figure 12:
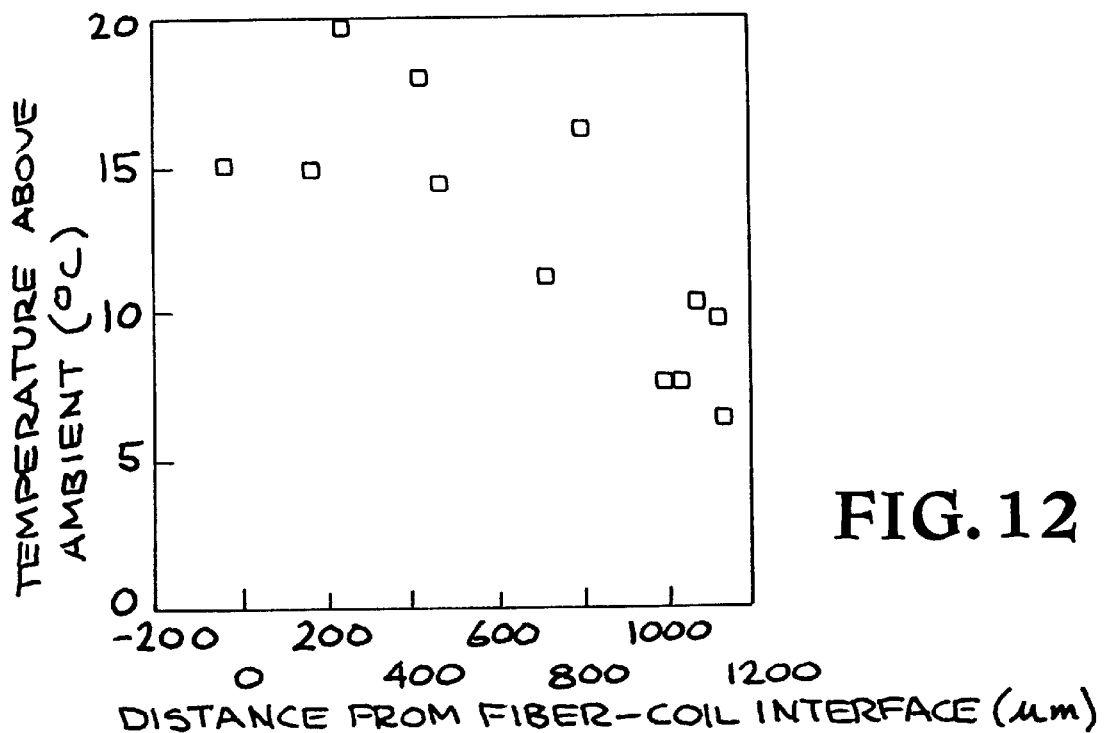
FIG. 12 graphically illustrates temperature distributions in the SMP material using the light coupling mechanism of FIG. 4.

FIG. 12 graphically illustrates temperature distributions in the SMP microgripper for the basic coupling technique of FIG. 4, show Trial #1 and Trial #2 at a higher power than Trial #1. The data for Trial #1, for example, shows that the temperature rise is within a 5° range through the first 800 $\mu$m of the SMP material. A thermal image has been produced which shows the highest temperature at the optic fiber-coil interface, with heat being transmitted along the end 45 of the SMP microgripper 40 of FIG. 4 toward the distal thereof.

FIG. 13 graphically shows proof-of-principle data for sensing the movement of the load or coil using the basic light coupling technique of FIG. 4. As shown in FIG. 1, a diode laser operating at a wavelength of 810 nm was coupled into the SMP microgripper. The SMP material had an absorption coefficient of 10 cm$^{-1}$. Thus the 1 mm penetration depth was sufficiently small to allow the SMP material to be near-uniformly heated such that the SMP material around the coil relaxed to its extruded diameter, as shown in FIG. 3. The continuous wave power delivered to the SMP microgripper was 50 mW. The reflection of this light energy was measured by the photodetector and plotted in FIG. 13. Note that this experiment was performed in air rather than in a fluid. The data show that the DC value of the reflected light changes by 34 percent relative to the nominal reflection that is present from the summation of reflections that occur at the different optic fiber connections and in the microgripper optic-fiber-air interface. FIG. 13 presents two near-identical curves, demonstrating that the reflection change is repeatable.

It has thus been shown that the present invention provides an SMP microgripper release system with release sensing to confirm release of the load from the microgripper. The release system and the release sensing to confirm release of the load (embolic coil) is accomplished utilizing a light source (laser), optic fibers, an optic coupler, and a photodetector. Thus, as the distance from the optic fiber-coil interface in the SMP microgripper increases, the reflected light decreases, which is detected by the photodetector. The sensing system of the invention, in addition to confirming the release of the coil or other load, which can be relayed to a display panel, can also be utilized to control the driving electrons of laser light source. The invention also encompasses various techniques for enhancing light coupling from the optic fiber secured in one end of the SMP microgripper into the SMP material retaining the coil, whereby release of the coil is accomplished in seconds rather than minutes, as in prior known coil/guidewire release systems. Thus the present invention provides a means for depositing a load in a remote location and confirming that the load is released from the microgripper at a desired point of use. While the invention has been described for medical applications, such as for depositing embolic coils for treatment of human brain aneurysms, it can be utilized in any application requiring remote deposition of an object.

While the invention has been described as a microgripper for use in small diameter (250 μm to 2 mm) passageways, such as arteries in the human body, the feedback principle of the invention can be utilized for any remote application regardless of size of the passageway and SMP gripper.

While the fiber optical coupler 24 is preferred, a light splitter may be used to direct a large portion of the laser light beam toward the SMP gripper and a small portion to the detector, thereby forming an air coupling arrangement.

While a particular embodiment of a deposition, release, and feedback system, along with examples of light coupling enhancement techniques, have been described and illustrated to exemplify and teach the principles of the invention, such are not intended to be limiting. Modifications and changes may become apparent to those skilled in the art, and it is intended that the invention be limited only by the scope of the appended claims.

The invention claimed is:

1. A combination comprising:
   An SMP gripper for retaining and releasing an object to be deposited at a point of use,
   means for causing release of such an object from said gripper, and
   means for sensing release of such an object from said gripper.

2. The combination of claim 1, wherein said means for causing release includes a light source and an optic fiber assembly connecting said light source to said gripper.

3. The combination of claim 2, wherein said means for sensing release includes said light source and said optic fiber assembly and additionally includes an optic fiber coupler or air coupler arrangement mounted in said optic fiber assembly and a photodetector operatively connected to said optic fiber coupler or air coupler arrangement.

4. The combination of claim 3, wherein said means for sensing release additionally includes a display panel operatively connected to said photodetector.

5. The combination of claim 3, wherein said means for sensing release, additionally includes a second photodetector operatively connected to said optic fiber coupler, said second photodetector being operatively connected to means for monitoring and/or controlling said light source.

6. The combination of claim 5, wherein said light source comprises a laser, and wherein each of said photodetectors are operatively connected to said optic fiber coupler by at least one fiber optic.

7. The combination of claim 6, additionally including a catheter, said gripper being mounted at one end of said catheter, and wherein said optic fiber assembly includes at least one optic fiber extending through said catheter and secured in one end of said gripper.

8. The combination of claim 7, additionally including an embolic coil comprising an object to be retained and released from said gripper.

9. The combination of claim 8, wherein said means for causing release of said coil incudes means for enhancing passage of light from said optic fiber to said gripper.

10. The combination of claim 9, wherein said means for enhancing passage of light is selected from the group consisting of providing a gap between said optic fiber and said coil, removing cladding from an end of the optic fiber, providing the gripper with a coating of reflective or low-refractive index material, providing the gripper with a graded dye, enlarging the end of the optic fiber, and providing a conical insert between the end of the optic fiber and the coil.

11. An object release and object release sensing system for an SMP microgripper comprising:
   a light source,
   an SMP microgripper retaining an object to be released in an end section thereof,
   an optic fiber assembly interconnecting said light source and said SMP microgripper,
   an optic fiber coupler mounted in said optic fiber assembly,
   means for sensing release of an object including at least one photodetector coupled to said optic fiber coupler by at least one optic fiber,
   whereby light from said light source passes through said optic fiber assembly to said SMP microgripper causing heating of at least said end section of said SMP microgripper causing release of said object therefrom, and wherein light reflected from an interface of said object and said fiber optic assembly passes through said optic fiber coupling to said at least one photodetector whereby release of the object from the microgripper is confirmed by the intensity of the reflected light.

12. The system of claim 11, wherein said light source is selected from the group consisting of continuous and pulsed light sources.

13. The system of claim 12, wherein said light source is a laser.

14. The system of claim 11, wherein said optic fiber assembly includes a plurality of optic fibers interconnected by optic fiber connectors.

15. The system of claim 11, wherein said optic fiber assembly includes an optic fiber located in a catheter and said optic fiber having one end secured in said SMP microgripper.

16. The system of claim 15, wherein said end of said optic fiber and said object retained in said SMP microgripper define an interface via which light from said light source is directed into said end section of said SMP microgripper causing expansion thereof and release of said object.

17. The system of claim 11, additionally including means for enhancing light coupling from said optical fiber assembly into said end of said SMP microgripper selected from the group consisting of providing a gap between an end of said optic fiber assembly and said object, removing cladding from an end of said optic fiber assembly, coating said SMP microgripper with reflective or low refractive index material, incorporating a graded dye along a length of said SMP microgripper, enlarging an end of said optic fiber assembly, and inserting a conical member between said optic fiber assembly and said object.

18. The system of claim 11, wherein said object comprises an embolic coil, and wherein said SMP microgripper and a connecting section of said optic fiber assembly are constructed to operate in a passageway having a diameter of from less than about 500 µm to about 2 mm.

19. The system of claim 18, wherein said connecting section of said optic fiber assembly comprises at least one optic fiber located in a catheter.

20. The system of claim 11, wherein said at least one photodetector is operatively connected to at least one of a display panel and a control for said light source.

* * * * *